United States Patent
Hayik et al.

(10) Patent No.: US 10,722,710 B2
(45) Date of Patent: Jul. 28, 2020

(54) SECRETION CLEARANCE AND COUGH ASSIST

(71) Applicants: Moshe Hayik, Hod Ha-Sharon (IL); Ovadia Sagiv, Kiron (IL)

(72) Inventors: Moshe Hayik, Hod Ha-Sharon (IL); Ovadia Sagiv, Kiron (IL)

( * ) Notice: Subject to any disclaimer, the term of this patent is extended or adjusted under 35 U.S.C. 154(b) by 243 days.

(21) Appl. No.: 15/934,960

(22) Filed: Mar. 24, 2018

(65) Prior Publication Data

US 2019/0290904 A1    Sep. 26, 2019

(51) Int. Cl.

| A61N 1/36 | (2006.01) |
|---|---|
| A61N 1/04 | (2006.01) |
| A41B 1/08 | (2006.01) |
| A61N 1/02 | (2006.01) |
| A61B 5/00 | (2006.01) |
| A61B 5/08 | (2006.01) |

(52) U.S. Cl.
CPC ............. *A61N 1/3601* (2013.01); *A41B 1/08* (2013.01); *A61B 5/0002* (2013.01); *A61B 5/0823* (2013.01); *A61B 5/7435* (2013.01); *A61B 5/7475* (2013.01); *A61N 1/025* (2013.01); *A61N 1/0476* (2013.01); *A61N 1/0484* (2013.01); *A61N 1/36031* (2017.08); *A41B 2400/32* (2013.01)

(58) Field of Classification Search
CPC .. A61N 1/3601; A61N 1/0484; A61B 5/0823; A61B 5/0002
See application file for complete search history.

(56) References Cited

U.S. PATENT DOCUMENTS

| 2,711,729 | A | 6/1955 | Hofmann |
|---|---|---|---|
| 3,077,884 | A | 2/1963 | Batrow et al. |
| 4,827,935 | A | 5/1989 | Geddes et al. |
| 4,830,008 | A | 5/1989 | Meer |
| 6,463,327 | B1 | 10/2002 | Lurie et al. |
| 6,587,726 | B2 | 7/2003 | Lurie et al. |
| 7,363,086 | B1 | 4/2008 | Koh et al. |
| 8,233,987 | B2 | 7/2012 | Gelfand et al. |
| 8,467,876 | B2 | 6/2013 | Tehrani |
| 8,509,901 | B2 | 8/2013 | Tehrani |
| 8,706,236 | B2 | 4/2014 | Ignagni et al. |
| 8,934,977 | B2 | 1/2015 | Errico et al. |
| 9,037,247 | B2 | 5/2015 | Simon et al. |
| 9,375,571 | B2 | 6/2016 | Errico et al. |
| 9,399,134 | B2 | 7/2016 | Simon et al. |
| 9,555,260 | B2 | 1/2017 | Simon et al. |
| 2003/0195571 | A1 | 10/2003 | Burnes et al. |
| 2017/0027813 | A1 | 2/2017 | Bobey et al. |

*Primary Examiner* — Alyssa M Alter
(74) *Attorney, Agent, or Firm* — Craig W. Barber; The Law Office of Craig Barber

(57) ABSTRACT

A device operates for secretion clearance and cough assistance by means of transdermal stimulation of muscle groups including the pectoralis majoris, the serratus anterior, and the abdominal muscles. The various muscle groups may be stimulated in different ways: not just different pulse trains but in addition, different stimulations to accomplish different phases of clearance or cough assistance. In a first phase a vibration action provided by the muscles (for example the pectoralis and serratus) is used to encourage the motion of mucus and other secretions within airways. In a second phase, the abdominal muscles for example might be stimulated differently so as to cause not a vibration but instead a coughing action, especially to detect and assist a natural cough. The invention further teaches a zone stimulator large enough to span and stimulate major muscles or groups of large muscles effectively.

15 Claims, 15 Drawing Sheets

302

304

306

| | |
|---|---|
| TIME & DATE | 502 |
| MONITORING DATA, INHERENT | 504 |
| TYPE OF PULSE APPLIED | 506 |
| PULSE APPLIED DURATION | 508 |
| PULSE APPLIED FREQUENCY | 510 |
| PULSE APPLIED AMPLITUDE | 512 |
| MONITORING DATA, ASSISTED | 514 |

FIG. 8

SECRETION CLEARANCE AND COUGH ASSIST

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but reserves all copyright rights whatsoever. 37 CFR 1.71(d).

CROSS-REFERENCE TO RELATED APPLICATIONS

N/A

FIELD OF THE INVENTION

This invention relates generally to secretion clearance and assistance with coughing and specifically to non-implanted, non-mechanical, transdermal secretion clearance cough assistance.

STATEMENT REGARDING FEDERALLY FUNDED RESEARCH

This invention was not made under contract with an agency of the US Government, nor by any agency of the US Government.

BACKGROUND OF THE INVENTION

Build up of mucus, watery nasal secretions, phlegm and other bodily secretions in the human lungs/lung airways is a serious issue. In the US alone tens of millions of people every year suffer from breathing issues due to congested lung airways because there are a wide range of causes of such build ups. Chronic causes include a variety of diseases such as cystic fibrosis, asthma and COPD.

COPD (chronic obstructive pulmonary disease) impacts an estimated 30 million individuals in the US and is the third leading cause of death in the US, killing more than 130,000 people per year. COPD causes secretion buildup problems, exacerbated by the fact that COPD is usually seen in those with extensive damage to the airways and lungs due to long term smoking.

COPD is of particular interest in regard to coughing, in particular. A person with COPD may have problems with their abdominal muscles so that they have trouble coughing in an effective manner.

Another dangerous lung airway disease is Cystic Fibrosis. A defective gene in people with Cystic Fibrosis causes a thick, sticky buildup of mucus in the lungs, and in the pancreas, and even in other organs. In the lungs, the mucus clogs the airways and traps bacteria, leading to infections, extensive lung damage, and eventually respiratory failure. More than 30,000 people in the US are living with Cystic Fibrosis, and the majority of that population are minors under the age of 18.

Known machines for assisting people with Cystic Fibrosis do not allow children to wear the device simply because the device is too large. It would be preferable to provide a smaller, wearable machine, especially one small enough to be worn by children and yet allow a full range of activities. In addition, many types of machines rely upon electrodes implanted in the body and it would be preferable to provide a machine to children which does not require surgery and surgical implants.

Lung cancer in certain forms can cause mucus production to spike excessively, and painfully. Medications can cause excessive productions, allergies can, certain foods (dairy products, etc) can, and so on and so forth.

In addition to the serious, chronic long-term conditions discussed previously, short-term viral and bacterial infections such as the common cold and pneumonia and influenza (which once killed 50 to 100 million people in one single outbreak) can cause secretion buildups. The present invention is directed toward long-term problems such as COPD, but might be useful in therapy for short-term problems.

Unsurprisingly, medical and emergency workers have put a great deal of effort into trying to clear the human airways of bodily secretions which are benign in themselves (small amounts of mucus are produced by the throat constantly, and keep it moist and healthy) but which sometimes become dangerously excessive.

The excess secretions: the lungs are kept moist with a thin film of fluid to stop them drying out. When there is a chest infection or occasionally in other situations, this fluid increases and become thick or even putrid. In the normal situation, these secretions are removed by coughing but in the presence of chronic lung disease, this is not always possible. Although antibiotics may control the infection, they do not remove the secretions that occur. Some will be reabsorbed into the body but very thick ones will remain. It is important to remove the secretions to allow more effective breathing and increase the amount of oxygen getting into the body.

FIG. 1 is a perspective view of a PRIOR ART manual percussion method of mucus clearance 2. A wide number of techniques such as this have been tried over the centuries and presumably require no introduction. Even more extreme surgical procedures have been developed as well. These techniques to aid breathing or to clear mucus are not relevant to the present invention. Manual percussion techniques of chest physiotherapy have been used for a variety of diseases such as cystic fibrosis emphysema, asthma, and chronic bronchitis, to remove the excess secretions (also called mucus, phlegm, sputum) from inside the lungs. This treatments generally performed by physical therapists and respiratory therapists. Clearly this treatment has severe limitations in practicality and efficiency.

Mechanical/Pneumatic systems: in order to bypass dependency on Manual percussion techniques of chest physiotherapy, Mechanical/Pneumatic systems/chest compression devices have been developed to produce high frequency chest wall oscillations, and may be the most successful method of airway clearance developed prior to the present invention. However, the Mechanical/Pneumatic systems are very noisy and required large energy for the engines and blowers therefore are not energy efficient and require either electrical plug-ins, making them completely immobile, or a big battery for a few small hours of operation.

FIG. 2 is a perspective view of a PRIOR ART mechanical assistance device 4. This device, which effectively immobilizes the wearer, features a base unit, a portion worn on the chest, and a series of connections between them. Prior art mechanical device 4 is merely exemplary: devices are known which use not just pneumatic operation but other types of physical actuation of the lungs to assist with secretion clearance, or just to assist with ventilation, breathing, etc. This particular machine does not have a face mask depicted, but face masks are very common.

A newer method has been developed in recent decades for assisting with breathing, heart irregularities and so on. One example may be found in FIG. 3, which is a block diagram of a PRIOR ART implanted electrode method of stimulating the phrenic nerve. Prior art implanted electrode 6 (there may be several or just one) is implanted in the chest: it may be subdermal, or deep inside the thoracic cavity, it may be implanted to stimulate the heart or other muscles or it may be placed quite close to the phrenic nerve 8. The phrenic nerve 8 is frequently mentioned as being stimulated in prior art. Again, this machine may well deal with ventilation and simply not be relevant to the field of cough assistance.

Note that other implanted electrode devices may stimulate the diaphragm muscle so as to assist with breathing/ventilation, however, the present invention is about coughing assistance and does not stimulate the diaphragm anyway.

Pacemaker devices are an interesting analogy, although they do not deal with coughing assistance (indeed do not deal with ventilation anyway). A pacemaker device is not an artificial heart and thus is designed to assist the natural beating of the heart rather than to artificially impose heart operation.

Obviously implanting electrodes is very undesirable. Not only is a surgery required but the electrode is a foreign object in the body, with all the potential issues which may arise from that. The electrode cannot be easily checked or replaced, may degrade, and may be psychologically unwelcome to the patient.

Finally, although the phrenic nerve has proven to be a useful target for stimulation, it would be preferable to provide easier and more effective targets for stimulation.

It would be preferable to provide targets for cough assist stimulation which require no electrodes to be implanted at all.

It would further be preferable to provide a device and method of cough assisting which does not require or force the patient to cough but rather relies up on the bodies own cough reflex, assisting that natural autonomic cough mechanism rather than replacing it.

It would further be preferable to provide convenient control mechanisms so that not just medical professionals but patients themselves can monitor their own secretion clearance, coughing and other information and control it as necessary and practical.

It would further be preferable to provide a device and method which leaves the patient with a complete range of motion including mobility, uses small batteries, and allows essentially all normal activities.

It would further be preferable to provide a device and method which requires no face mask, no hoses, tubes or implanted electrodes. It would be preferable to provide a method which is fully electronic and yet requires no implantation or other surgery.

It would further be preferable to provide a device and method which operates by means of multiple different actions: small vibrations, larger muscle stimulations, options of different musculature usage and so on. Note that a diaphragm or heart stimulation technique by way of an implanted electrode has only a single choice of target, but the present invention is not so limited.

These and other aspects and objectives are addressed by the present invention.

SUMMARY OF THE INVENTION

General Summary

The present invention teaches a device which operates for secretion clearance and cough assistance by means of transdermal stimulation of muscle groups involved in secretion clearance and coughing. However the diaphragm muscle is not implicated. Muscles used in various phases include the pectoralis majoris, the serratus anterior, and the abdominal muscles. These are stimulated by pulse trains applied from electrode patches on the surface of the skin, without need for any implantation procedure at all.

It may be seen that the abdominal muscles come in various pairs or groups and that different combinations may be used depending on circumstances, efficiency and so forth. The same choices are allowed for the muscles of the chest when they are stimulated. Finally, the various muscle groups may be stimulated in different ways: not just different pulse trains but in addition, different stimulations to accomplish different phases of clearance or cough assistance.

The present invention teaches that the stimulation may be applied in two different phases or stages: 1. Stimulation in hi frequency vibration to create compressions against the chest wall to help remove mucus from breathing passages, and 2. Simulation of the Abdominal muscle augmenting/increasing the coughing ability needed to clear airways of secretions and irritants.

In the first phase (1) a vibration action provided by the muscles (for example the pectoralis and serratus) is used to encourage the motion of mucus and other secretions within various different sizes and locations of airways ranging from bronchii all the way up to the major airways or even throat.

In second phase (2), the abdominal muscles for example might be stimulated differently so as to cause not a vibration but instead a coughing action. Beneficially, the invention might even be used to supplement natural coughing action: the device of the invention may await a natural cough detection and promptly aid the action of the abdominal muscles (which are often damaged by COPD and other conditions) so that a more efficient cough is attained.

The disclosed method and system for Secretion Clearance and Cough Assist is in fact fully electronic with no mechanical or pneumatic part, and yet is highly effective at clearing the human lungs of mucus.

Yet it is also non invasive—no need for surgery and no need to simulate the spinal cord tracts. Furthermore it is silent and very energy efficient—can work using a small battery for a week and more.

The method and device is comprised of a special wearable part with electrodes (see FIG. 4) and control module that generate special patterns of signals (according to desired algorithms) which signals are sent to the electrodes. The device thus electrically transdermally stimulates directly the pectoralis major and serratus anterior muscles for secretion clearance and the abdominal muscles for cough assist.

The control module has a start button to start operations with present parameters, and includes wireless communication to a smart phone for display of data, results, and so on, not to mention allowing wireless setup, maintenance and control The control module may optionally include a small touch screen display for setup of the parameters and display of the results.

Muscle Physiology and the Response to Electronic Stimulation:

The muscle responds to a single electronic stimulation with a quick contraction and relaxation. The stimulus that results in a muscle twitch is based on the magnitude of the stimulus (voltage) and the rate at which stimuli are applied (frequency).

Magnitude of Electric Stimulation:

The strength of the twitch increases with the increase in the magnitude of the shock. Therefore, the strength of the twitch is said to be graded (or incrementally increased). This is due to the recruitment of increased numbers of muscle fibers that are involved in the twitch. Thus, an electronically assisted cough can in fact be physically stronger than an unassisted cough, and yet the augmentation or strengthening is entirely due to physical muscle action only.

Frequency of Electric Stimulation:

If the frequency of the shock is increased, the second stimulus will be applied before the first muscle twitch is over, then the second stimulus will build upon the previous contraction and add to that response. If the frequency will be increased more, eventually no relaxation will be allowed and the muscle contraction will increase smoothly up to a point of maximum strength.

Summary in Reference to Claims

It is therefore another aspect, advantage, objective and embodiment of the invention, in addition to those discussed previously, to provide a secretion clearance and cough assistance device for use by a patient having a body, skin, a mouth, airways, first, second, third, and fourth pairs of abdominal muscles, and chest muscles including pectoral muscles and serratus anterior muscles, such patient suffering from bodily secretions in such airways, the secretion clearance and cough assistance device comprising:

a control module having operative electrical connections to a plurality of dermal electrodes attached to such skin of such patient, the control module small enough to be worn on such patient body;

a first one of the dermal electrodes disposed on such skin of such patient at one such abdominal muscle;

a second one of the dermal electrodes disposed on such skin of such patient at one such chest muscle;

the control module having a stimulation module operative to send a first pulse train to such chest muscle and a second pulse train to such abdominal muscle;

the first pulse train operative to stimulate such chest muscle so as to cause a first vibration of such chest muscle, the vibration of such chest muscle thereby causing a second vibration of such airways;

the second pulse train operative to stimulate such abdominal muscle so as to stimulate at least one cough;

whereby the second vibration loosens such bodily secretions in such airways and the at least one cough moves such bodily secretions toward such mouth of such patient.

It is therefore another aspect, advantage, objective and embodiment of the invention, in addition to those discussed previously, to provide a secretion clearance and cough assistance device for use with a shirt worn on such body by such patient, wherein:

the control module, the dermal electrodes and the operative electrical connections are small enough to be worn on such body concealed within such shirt, and further comprising:

a garment worn about such body by such patient, the garment concealed within such shirt, and the garment concealing the control module, dermal electrodes and operative electrical connections within itself.

It is therefore yet another aspect, advantage, objective and embodiment of the invention, in addition to those discussed previously, to provide a secretion clearance and cough assistance device further comprising:

a third one of the dermal electrodes disposed on such skin of such patient at a second such abdominal muscle;

a fourth one of the dermal electrodes disposed on such skin of such patient at a third such abdominal muscle;

a fifth one of the dermal electrodes disposed on such skin of such patient at a fourth such abdominal muscle;

the control module further operative to send the second pulse train to such second, third and fourth abdominal muscles.

It is therefore another aspect, advantage, objective and embodiment of the invention, in addition to those discussed previously, to provide a secretion clearance and cough assistance device further comprising:

a sixth one of the dermal electrodes disposed on such skin of such patient at a second such chest muscle;

a seventh one of the dermal electrodes disposed on such skin of such patient at a third such chest muscle;

an eighth one of the dermal electrodes disposed on such skin of such patient at a fourth such chest muscle;

the control module further operative to send the first pulse train to such second, third and fourth chest muscles.

It is therefore another aspect, advantage, objective and embodiment of the invention, in addition to those discussed previously, to provide a secretion clearance and cough assistance device, the first pulse train further comprising:

a first group of pulses consisting of a plurality of individual pulses increasing in amplitude with time, the first group of pulses having a duration of 20 to 80 ms;

a first time out period of 20 ms-250 ms during which no pulses are sent;

repetitions of the first group of pulses and the first time out period for a vibration time period.

It is therefore another aspect, advantage, objective and embodiment of the invention, in addition to those discussed previously, to provide a secretion clearance and cough assistance device, the second pulse train further comprising:

a second group of pulses consisting of a plurality of individual pulses increasing in amplitude with time, the second group of pulses having a duration of 500 ms to 900 ms;

a second time out period of 2 to 3 seconds during which no pulses are sent;

repetitions of the second group of pulses and the second time out period for a cough assist time period defined to last either until an autonomic cough occurs or for a period of time of no more than 10 seconds.

It is therefore another aspect, advantage, objective and embodiment of the invention, in addition to those discussed previously, to provide a secretion clearance and cough assistance device, further comprising:

at least one sensor of at least one physiological parameter;

the at least one sensor being a cough sensor, the cough sensor in operative communication with the control module, the cough sensor disposed on such skin of such patient; the control module further comprising an analysis module operative to receive a data from the cough sensor and analyze the data to determine if such patient is exhibiting an autonomic cough and if such patient is exhibiting an autonomic cough, the control module further operative to send the first pulse train.

It is therefore another aspect, advantage, objective and embodiment of the invention, in addition to those discussed previously, to provide a secretion clearance and cough assistance device, further comprising:

an RF communication module;

a mobile device having an operative RF connection to the RF communication module of the control module;

the mobile device having a module operative to provide wireless control of the operation of the control module;

the mobile device operative to collect data, provide for wireless setup and wireless maintenance of the secretion clearance and cough assistance device.

It is therefore another aspect, advantage, objective and embodiment of the invention, in addition to those discussed previously, to provide a secretion clearance and cough assistance device, further comprising:

the control module having a non-volatile memory and a central processor unit, the analysis module stored in the non-volatile memory.

It is therefore another aspect, advantage, objective and embodiment of the invention, in addition to those discussed previously, to provide a secretion clearance and cough assistance device, wherein the control module further comprises:

a touch screen operative to display a set of data collected by the device and enable control of the secretion clearance and cough assistance device.

It is therefore another aspect, advantage, objective and embodiment of the invention, in addition to those discussed previously, to provide a secretion clearance and cough assistance device, wherein the control module has a start button operative to activate the secretion clearance and cough assistance device to begin an operating cycle, using a first set of preset operating parameters stored in the non-volatile memory;

the start button further operative to establish the operative RF connection to the mobile device.

It is therefore another aspect, advantage, objective and embodiment of the invention, in addition to those discussed previously, to provide a secretion clearance and cough assistance device, wherein the mobile device is operative to provide control of the control module by one mode selected from the group consisting of: manual control input to the mobile device and the control module, manual control input to the mobile device and from the mobile device to the control module, adaptive heuristic control by an artificial intelligence module loaded in the mobile device and the control module, adaptive heuristic control by an artificial intelligence module loaded in the mobile device and from the mobile device to the control module, remote control from a remote location via communication with the mobile device and from the mobile device to the control module, and combinations thereof.

It is therefore another aspect, advantage, objective and embodiment of the invention, in addition to those discussed previously, to provide a cough assistance device for use by a patient having skin, a mouth, airways, and first, second, third, and fourth pairs of abdominal muscles, such patient suffering from bodily secretions in such airways, the cough assistance device comprising:

a control module having operative electrical connections to a plurality of dermal electrodes attached to such skin of such patient;

a first one of the dermal electrodes disposed on such skin of such patient at one such abdominal muscle;

the control module having a stimulation module operative to send a pulse train to such abdominal muscle;

the pulse train operative to stimulate such abdominal muscle so as to stimulate at least one cough;

whereby the at least one cough moves such bodily secretions toward such mouth of such patient.

It is therefore another aspect, advantage, objective and embodiment of the invention, in addition to those discussed previously, to provide a cough assistance device further comprising: a second one of the dermal electrodes disposed on such skin of such patient at a second such abdominal muscle;

a third one of the dermal electrodes disposed on such skin of such patient at a third such abdominal muscle;

a fourth one of the dermal electrodes disposed on such skin of such patient at a fourth such abdominal muscle;

the control module further operative to send the pulse train to such second, third and fourth abdominal muscles.

It is therefore another aspect, advantage, objective and embodiment of the invention, in addition to those discussed previously, to provide a cough assistance device further comprising: a cough sensor, the cough sensor in operative communication with the control module, the cough sensor disposed on such skin of such patient;

the control module further comprising an analysis module operative to receive a data from the cough sensor and analyze the data to determine when such patient is exhibiting an autonomic cough and when such patient is exhibiting an autonomic cough, the control module further operative to send the pulse train.

It is therefore another aspect, advantage, objective and embodiment of the invention, in addition to those discussed previously, to provide a method of secretion clearance and cough assistance for use by a patient having skin, a mouth, airways, first, second, third, and fourth pairs of abdominal muscles, and chest muscles including pectoral muscles and serratus anterior muscles, such patient suffering from bodily secretions in such airways, the secretion clearance and cough assistance, comprising the steps of:

sending a first pulse train controlled by a first set of parameters to a first electrode disposed on such skin of such patient at one such chest muscle, the first pulse train operative to stimulate such chest muscle so as to cause a first vibration of such chest muscle, the vibration of such chest muscle thereby causing a second vibration of such airways;

whereby such second vibration loosens such bodily secretions in such airways;

sending a second pulse train to a second electrode disposed on such skin of such patient at a first such abdominal muscle, the second pulse train operative to stimulate such abdominal muscle so as to stimulate at least one assisted cough;

whereby the at least one assisted cough moves such bodily secretions toward such mouth of such patient.

It is therefore another aspect, advantage, objective and embodiment of the invention, in addition to those discussed previously, to provide a method of secretion clearance and cough assistance further comprising:

monitoring such patient and sending a data set to an analysis module;

determining by means of the analysis module when such patient is exhibiting an autonomic cough and when such patient is exhibiting an autonomic cough, sending the first pulse train.

It is therefore another aspect, advantage, objective and embodiment of the invention, in addition to those discussed previously, to provide a method of secretion clearance and cough assistance further comprising:

wirelessly accessing the analysis module from a remote location; and providing the data set to the remote location.

It is therefore another aspect, advantage, objective and embodiment of the invention, in addition to those discussed previously, to provide a method of secretion clearance and cough assistance further comprising:

wirelessly altering the first set of parameters from the remote location.

It is therefore another aspect, advantage, objective and embodiment of the invention, in addition to those discussed previously, to provide a secretion clearance and cough assistance device for use by a patient having a body, skin, a mouth, airways, first, second, third, and fourth pairs of abdominal muscles, and chest muscles including pectoral muscles and serratus anterior muscles, such patient suffering from bodily secretions in such airways, the secretion clearance and cough assistance device comprising:

a control module having operative electrical connections to a plurality of zone group stimulators attached to such skin of such patient, the control module small enough to be worn on such patient body;

a first one of the zone group stimulators disposed on such skin of such patient at at least one such chest muscle;

a second one of the zone group stimulators disposed on such skin of such patient at at least one such abdominal muscle;

the control module having a stimulation module operative to send a first pulse train to such chest muscle and a second pulse train to such abdominal muscle;

the first pulse train operative to stimulate such chest muscle so as to cause a first vibration of such chest muscle, the vibration of such chest muscle thereby causing a second vibration of such airways;

the second pulse train operative to stimulate such abdominal muscle so as to stimulate at least one cough;

whereby the second vibration loosens such bodily secretions in such airways and the at least one cough moves such bodily secretions toward such mouth of such patient.

It is therefore another aspect, advantage, objective and embodiment of the invention, in addition to those discussed previously, to provide a secretion clearance and cough assistance device, the first pulse train further comprising:

a first group of pulses consisting of a plurality of individual pulses increasing in amplitude with time, the first group of pulses having a duration of 20 to 80 ms; a first time out period of 20 ms-250 ms during which no pulses are sent;

repetitions of the first group of pulses and the first time out period for a vibration time period;

the second pulse train further comprising:

a second group of pulses consisting of a plurality of individual pulses increasing in amplitude with time, the second group of pulses having a duration of 500 ms to 900 ms; a second time out period of 2 to 3 seconds during which no pulses are sent;

repetitions of the second group of pulses and the second time out period for a cough assist time period defined to last either until an autonomic cough occurs or for a period of time of no more than 10 seconds.

BRIEF DESCRIPTION OF THE DRAWINGS

FIG. 8 is a simple data structure as might be used by the device to assist therapeutic activities, to test the device or to optimize usage of the device for a given patient or condition.

FIG. 11 followed by FIG. 12.

INDEX TO REFERENCE NUMERALS

Figure 1:
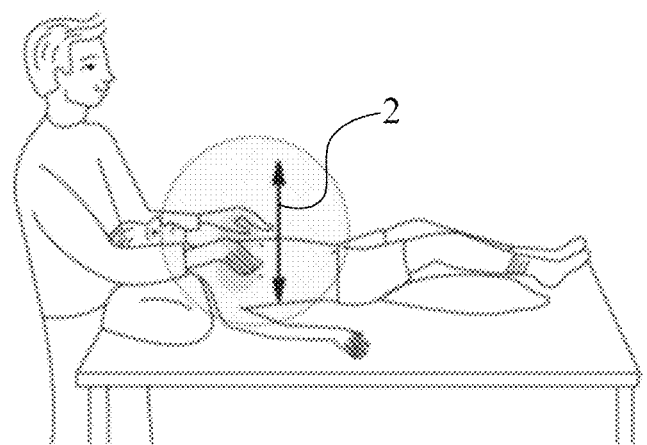
FIG. 1 is a perspective view of a PRIOR ART manual percussion method of mucus clearance.

Prior art manual percussion 2
Prior art mechanical device 4
Prior art implanted electrode 6
Phrenic nerve stimulated in prior art 8
Patient 100
System 102
Pectoralis major 104
Serratus anterior 106
Abdominal muscles 108
Dermal electrode pads 110
Leads 112
Control module 114
RF connection (Bluetooth®, Wifi, etc) 116
Mobile device (smart phone) 118
Autonomic cough detector 120
Vibration phase 202
Vibration time 204
Cough phase 206
Sense cough 208
Cough or time out? 210
Assisted cough 212
Exemplary pulse trains 302, 304, 306
System 400
Operating system 402
Power management 404
Controller unit 406
Wired communication 408
Processor (CPU) 412
Optional display screen control 414
Cough monitor 416
Analysis module 418
Stimulation control module 420
RF communication (such as Bluetooth®/Wifi) 422
Mobile device 424

Control module 426
App display module 428
App user input control module 430
User history module 432
Help module 434
Event 500
Time&Date 502
Autonomic cough monitored data 504
Pulse train stimulation applied type 506
Pulse train stimulation applied duration 508
Pulse train stimulation applied frequency 510
Pulse train stimulation applied amplitude 512
Assisted cough monitored data
Shirt 900
Dermal electrode pads 910
Leads 912
Control module 914
Monitor 920
Garment 1360
Patient 1400
Control module 1414
Sensor/monitor 1420
Zone "A" (pectoralis) stimulator pad 1472
Zone "B" (serratus) stimulator pad 1474
Zones "C" and "D" (abdominal) stimulators 1476
Patient 1500
Pectoralis major 1504
Serratus anterior 1506
Abdominal muscles 1508
Dermal zone stimulation pads 1510
Leads 1512
Control module 1514
RF connection (Bluetooth®) 1516
Mobile device (smart phone)

DETAILED DESCRIPTION

Glossary

A secretion as used herein refers to an internal bodily secretion, including but limited to: mucus, nasal drip, phlegm, and other liquid and semi-liquid excretions which occur in human airways.

As used herein the word cough carries its ordinary meaning. An autonomic cough however refers to a cough which occurs naturally, due to normal internal processes such as irritation of an airway. This is distinguished from coughs which may be deliberately triggered by the invention. Promoting a cough refers to either or both of a) increasing the power of an autonomic cough by detecting it and applying electrical stimulation to abdominal muscles so as to increase the number of muscle fiber bundles which contribute force to the cough, (also called herein an "assisted cough", and/or b) causing a cough deliberately by means of the invention.

Skin, mouth, abdominal muscles, and chest muscles including pectoral muscles and serratus anterior muscles all have their ordinary meanings Note that all such muscles may be stimulated transdermally ("through the skin") by placement of a dermal ("on the skin") electrode which electrode does NOT itself need to be implanted in the skin. Such electrodes may be attached by adhesives designed to hold well to human skin and yet promote electrical transmission between electrode and skin.

As used herein "airways" refers to the respiratory system passages which allow air to enter and leave the human body, including, but not limited to, the trachea, bronchus, bronchi, bronchiole, alveoli, as well as to anatomical features which allow air flow but can become congested with secretions: mouth, nasal passages, the esophagus, voice box and vocal cords, etc, etc.

As used in the claims attached herein, the word "such" indicates parts or aspects of a human patient and are pre-ambular language.

The present invention teaches zone stimulator pads which cover a substantial part of a muscle group: a zone electrode may have one, or preferrably more than one large enough electrode(s) within it as an inner layer. The large electrodes within the zone electrode may be in direct touching contact with the skin and be inside of a large fabric enclosure. The fabric forms a second layer on the outside of the electrodes, insulating the electrodes (the fabric has insulating properties) from contact with shirts, other body parts, etc.

The zone stimulators of the invention may in fact stimulate a "group" of muscles, or a large muscle over a considerable area of the muscle rather than a single point (thus acting like a group of electrodes) and thus the term "zone group stimulators" is also used interchangeably with the term zone stimulators.

As used herein, a "first" pulse train may be the pulses applied to the chest to loosen secretions, while a "second" pulse train may be the pulses applied to the abdominal muscles to assist coughing. However, this designation is for clarity. In practice, the first pulse train being applied before the second is preferred, but the cycle repeats and thus this designation becomes somewhat arbitrary.

End Glossary

Figure 2:
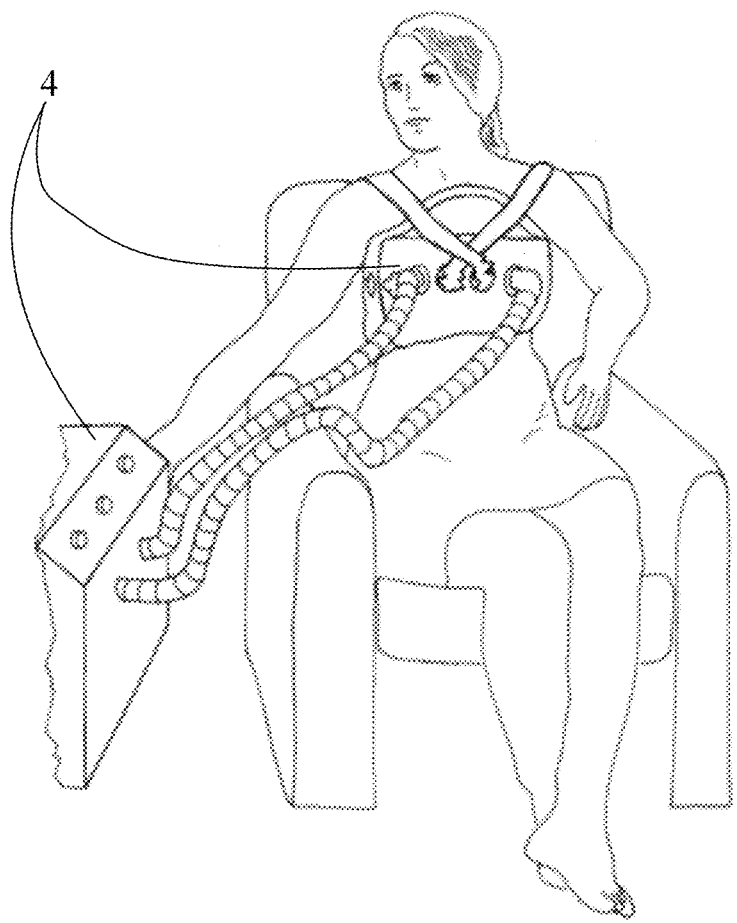
FIG. 2 is a perspective view of a PRIOR ART mechanical assistance device.
Figure 3:
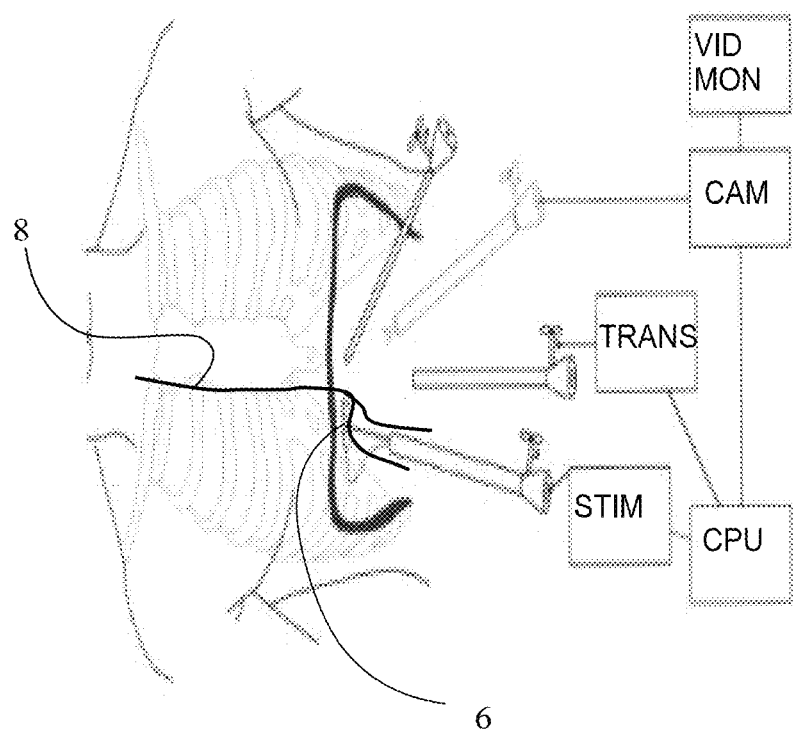
FIG. 3 is a block diagram of a PRIOR ART implanted electrode method of stimulating the phrenic nerve.

FIG. 1 is a perspective view of a PRIOR ART manual percussion method of mucus clearance, while FIG. 2 is a perspective view of a PRIOR ART mechanical assistance device and FIG. 3 is a block diagram of a PRIOR ART implanted electrode method of stimulating the phrenic nerve, all as discussed previously in the BACKGROUND section of the present application.

Figure 4:
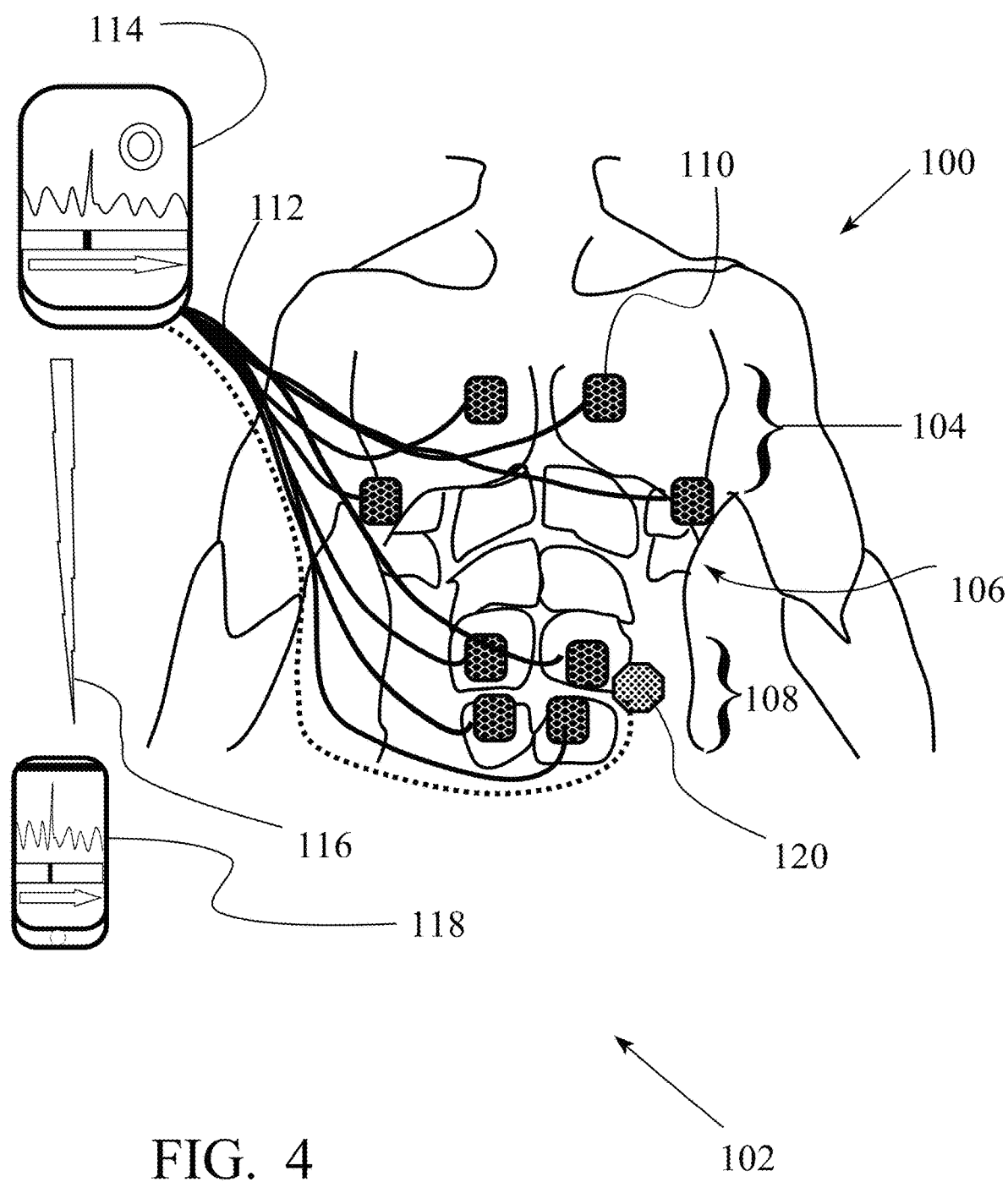
FIG. 4 is an overview block diagram of the first embodiment of the present invention showing relevant muscle groups, lack of implants, dermal electrodes and sensors, the control module and a mobile device which serves as control and input/output for the device.

FIG. 4 is an overview block diagram of the first embodiment of the present invention showing relevant muscle groups, lack of implants, dermal electrodes and sensors, the control module and a mobile device which serves as control and input/output for the device.

Patient 100 is attached to system 102 by leads 112 to dermal electrode pads 110, which are placed on the surface of the patient's skin.

The location of the dermal electrode pads is important, as the dermal electrode pads 110 will be used to transmit signals through the skin (transdermally) to the underlying muscles. Thus pads which are properly placed over the muscles of interest will activate the desired muscles. Two pads are shown located on the pectoralis major 104 muscles of the upper front chest, while two more pads are shown over the serratus anterior 106 chest muscles (note that in a two dimensional diagram it may be hard to see the three dimensional layout of the musculature).

The chest muscles tend to be implicated in breathing, that is, to draw breath a human autonomic system with expand the diaphragm downward and the chest muscles outward, while to exhale the automatic reflex is to compress the chest muscles inward and squeeze the diaphram upward into the chest cavity. In this case however, the diaphragm is not shown and the phrenic nerve is not shown as they are totally uninvolved in the present invention, which teaches an alternative to their usage. The chest muscles are shown, but the present invention utilizes them for purposes other than inhalation and exhalation, another unique aspect of the invention.

Finally, abdominal muscles 108 may all have, or some may have dermal electrode pads 110 as well. There are a large number of abdominal muscles, these are implicated in coughing action.

The present invention teaches that electrodes may be placed over the chest muscles (in particular the pectoralis and serratus discussed above) to activate these muscles, but for vibration rather than for breathing. Thus literature teaching stimulation of these muscles for breathing (inhalation and exhalation) is in fact teaching away from their mode of employment herein.

The vibration of the muscles (a first vibration) will turn cause a second vibration of the entire respiratory system (with the exception of those parts located inside the head) and the airways of the system. This second vibration, the vibration of the airways, will act to gently loosen up secretions within the system, for example, clinging to the walls of the air passages, or trapped in smaller bronchiolea, and throughout the system at most sizes of airways.

The abdominal muscles are stimulated in a different way. The abdominal muscles are stimulated to promote coughing. As noted previously, "promote" in this application means either causing an artificially induced cough, or, by activating musculature (in particular muscle bundles) while an autonomic ("natural") cough is occurring, it increases the number of muscle fiber bundles available and used in the cough, thus increasing the power of the cough.

In use in a preferred embodiment and best mode presently contemplated, the vibration may first be induced for a period of time, and then one or more coughs induced. In a second and also preferred embodiment and best mode presently contemplated, instead of inducing artificial coughs, the system awaits an autonomic cough and then stimulates the abdominal muscles to promote the autonomic cough by strengthening it. In alternative embodiments, it may be found efficient to have the vibration happen concurrently with the coughing or perhaps even after, or there may be multiple rounds of vibration for each cough, and so on.

Leads 112 lead to control module 114. Control module 114 will be discussed further in reference to FIG. 7, but in summary has a number of modules or physical machines which are able to control the activation of the electrodes and cause mild electrical charges to be applied thereby.

RF connection (such as Bluetooth®, Wifi, or other equivalents) 116 in turn connects the control module 114 to a mobile device 118, which may be a smart phone, an iPhone, an Android phone, or it may be a tablet or music player or pod, a tablet PC, a laptop or netbook or other similar device. The mobile device 118 has a "control module" (meaning a programmed function) which controls the "control module" (114, meaning the hardware device connected to and controlling the electrodes).

Finally autonomic cough detector 120 may optionally be employed to detect autonomic coughs (that is coughs which the body generates without artificial stimulation), and it may also be used to monitor breathing, to monitor the efficiency of different types, frequencies, amplitudes and wave forms of stimulation, and transmit data collected on patient coughs, breathing, and so on, to the control module 114.

Figure 5:
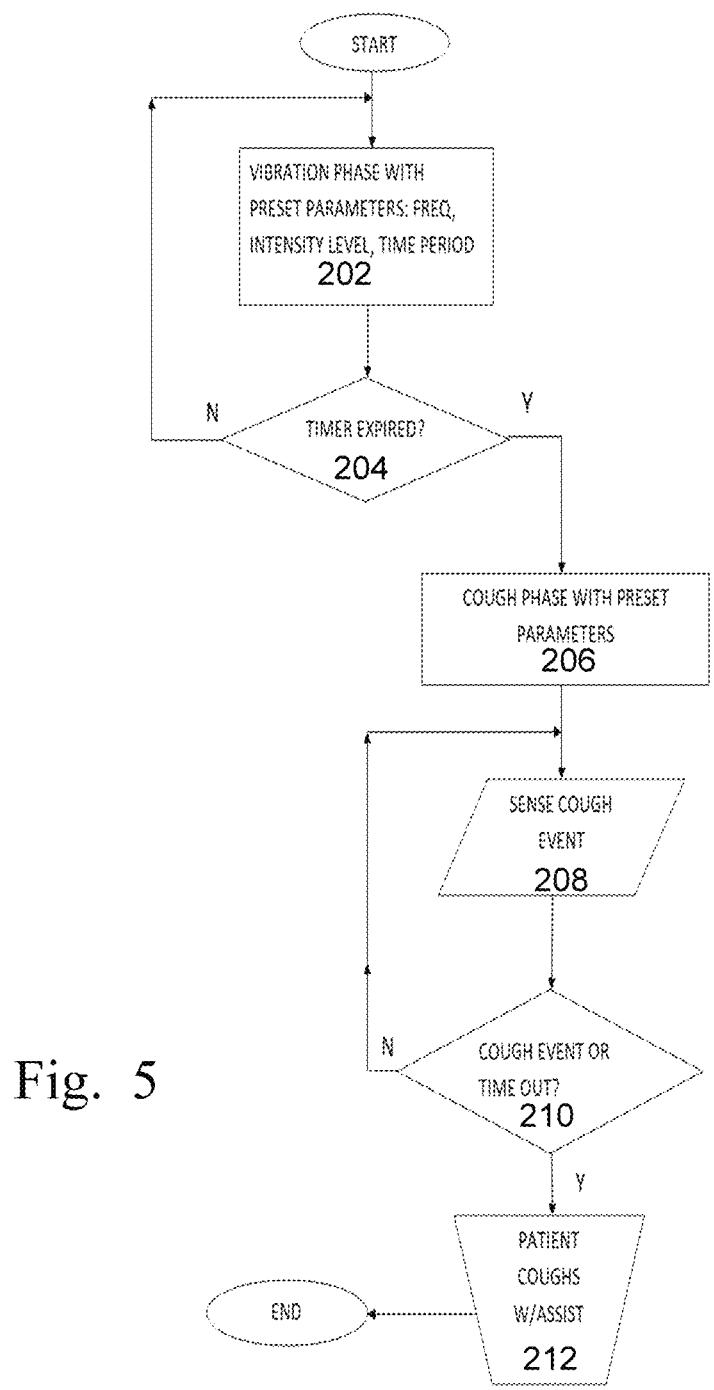
FIG. 5 is a flowchart of the second embodiment of the invention, showing the steps of the method.

FIG. 5 is a flowchart of the second embodiment of the invention, showing the steps of the method. Vibration phase 202 involves the control module sending pulse trains to the electrodes emplaced on the chest muscles (pectoralis/serratus) and thus stimulating them to vibrate, loosening internal bodily secretions. This is done with a series of short pulse trains, as will be discussed immediately after this (using FIG. 11). After a set vibration time 204 (for example, 20 minutes) a cough phase 206 commences, in which the device attempts to sense a cough (step 208), and if no autonomic cough occurs by a time out period 210, then the invention stimulates an assisted cough 212. This is done by means of a series of noticeably longer pulse trains applied not to the chest muscles but to the abdominal muscles instead. This phase will be discussed immediately after this, in regard to FIG. 12.

Importantly the device may have an algorithm which analyzes the monitored data, and examines the stimulation history, and based upon the algorithm, then actually optimizes the parameters of the stimulation, thus providing a unique and optimized stimulation from moment to moment or from cough to cough.

Figure 11:
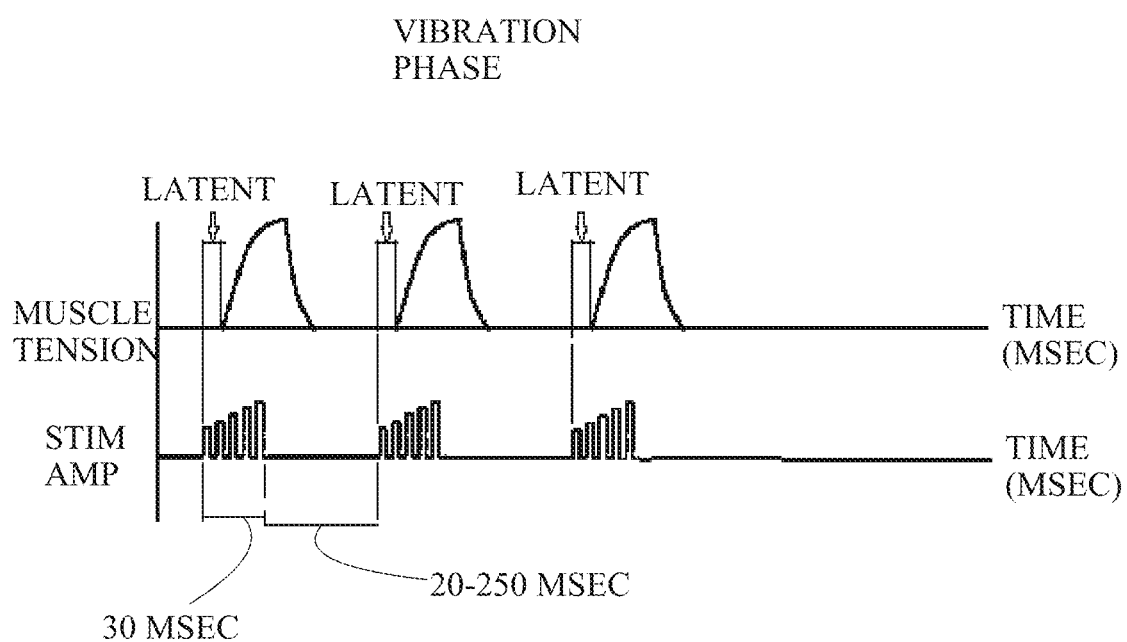
FIG. 11 is a pulse train sequence applied to the chest muscles to induce vibration of the muscles and thus loosening of secretions.
Figure 12:
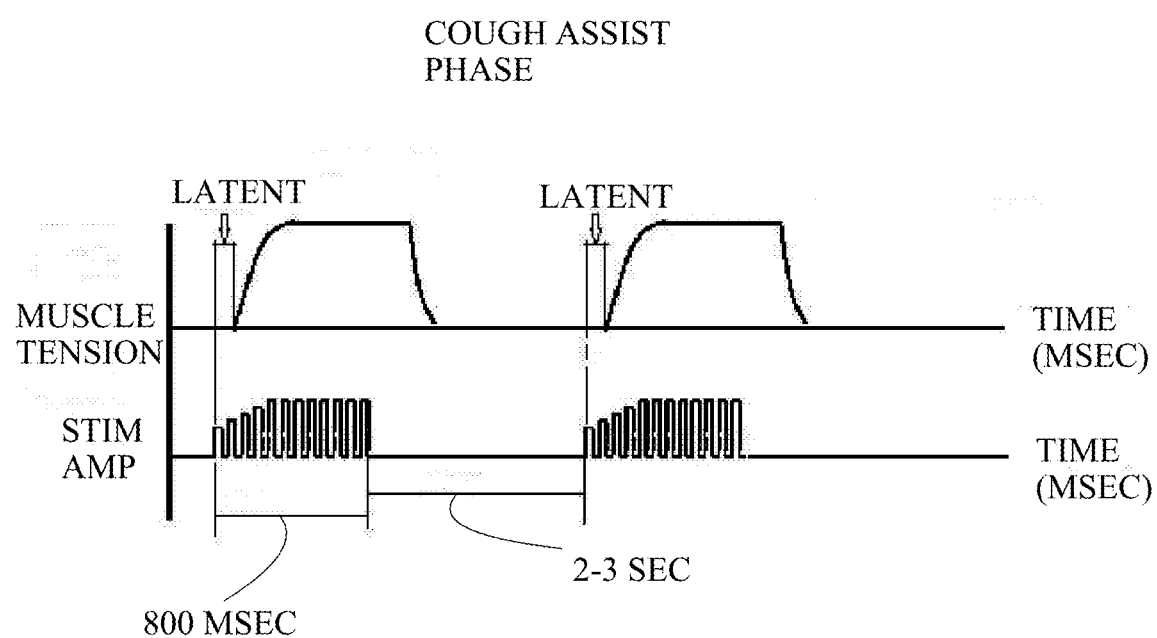
FIG. 12 is a pulse train sequence applied to the abdominal muscles to assist coughing. Note that FIGS. 11 and 12 may in some embodiments form a single sequence.

FIG. 11 is a pulse train sequence applied to the chest muscles to induce vibration of the muscles and thus loosening of secretions, referred to herein as a "first" pulse train. FIG. 12 is a pulse train sequence applied to the abdominal muscles to assist coughing, referred to herein as a "second" pulse train. Note that FIGS. 11 and 12 may in some embodiments form a single sequence: FIG. 11 followed by FIG. 12. Since the cycle repeats, the designation of "first" and "second" is somewhat arbitrary after the first pulse train is finished.

FIG. 11 shows (on the lower horizontal axis) the stimulation applied to the chest muscles during the vibration phase, when the muscles are stimulated into vibration to shake loose secretions from lung and breathing airways. A 30 millisecond series of pulses (perhaps about 3 ms per individual square pulse) are applied. A brief period of muscle latency follows: for a few milliseconds the muscle does not respond, as shown on the upper axis (muscle tension), which does not instantly respond.

The latency period quickly ends and the muscle tension builds up (see the "shark-fin" response curve). Thus, the stimulation amplitude axis shows the "input" to the patient's chest muscles, and the muscle tension horizontal axis shows the resultant/output tension detected in the patient's muscles. (The time scales of the two horizontal axes are the same, both zero origin and equally spaced milliseconds.)

The amplitude of the individual pulses of the train may be seen to steadily increase so as to efficiently promote increased muscle tension.

After this very short stimulation period (30 msec is presently preferred but times from 20 milliseconds or less up to 60 milliseconds or more may still function), a time out period ensues. The control module ceases sending the stimulation pulses to the electrode pads of the chest muscles and the muscles relax, for a period which may range from 20 to 250 milliseconds.

The cycle may advantageously repeat at this point. In FIG. 11 only 3 repetitions of the cycle (three series of multiple pulses causing three "shark fin" shaped muscle tension graphs) are shown, however, in reality the number may be variable, smaller or much much larger, 10, 20, 30 minutes or more for the entire vibration phase.

Note that the clearance of secretions will move them around and inevitably result in different physical sensations in the airways, which may cause a "natural" cough. In that event, the invention may sense the impending cough and act to promote that autonomic cough with abdominal stimulation.

After a preset or otherwise determined period of time, or in response to other input, the invention may move from the vibration phase of FIG. 11 to the cough assist phase of FIG. 12.

In this phase, the invention begins to stimulate the cough involved muscles, such as the abdominal muscles, and may cease stimulating the chest muscles temporarily. Once again the stimulation pulse train is applied, however, the abdominal muscles are stimulated for a considerably longer time: perhaps 500 to 900 milliseconds, presently preferred to be 800 milliseconds, although longer and shorter times may be used in embodiments. Once again, a latent period occurs (this time in the abdominal muscles not the chest muscles, which are not depicted upon this graph of FIG. 12), but then the tension in the abdominal muscles begins to increase. Note that the response graph of measured tension is a somewhat different shape, due to the prolonged period of stimulation: the period of maximal tension is now prolonged, for example, it may be 750-800 milliseconds during which the abdominal muscle tension is maximized.

This in turn has the effect of increasing the chances that the patient will cough, and if the patient does cough, the muscle tension artificially built up in the abdominal muscles will add to the power of the cough. It is important to understand that a muscle which has had the stimulation applied and has tensed up is likely to demonstrate a stronger cough than a muscle which has not been treated. Combined with the earlier vibration phase in which secretions are loosened and moved around, the result can be a stronger cough which produces more motion of the secretions and thus much greater clearance.

In the presently preferred embodiment, the invention will use a series of square pulses, followed by breaks. However, it is not limited to the longer pulse train waveforms addressed above. The invention pulse trains are in fact carefully calibrated based upon experimentation. These pulse trains in turn are composed of numerous smaller individual pulses.

Figure 6A:
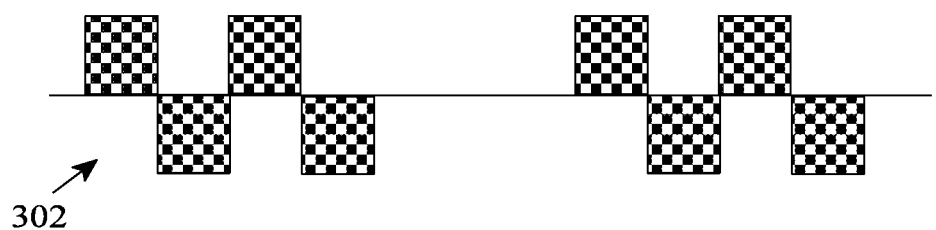
FIGS. 6A, 6B, and 6C are diagrams of exemplary pulse trains such as the invention might employ.
Figure 6B:
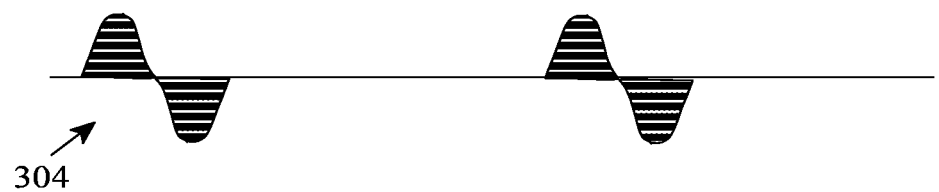
Figure 6C:
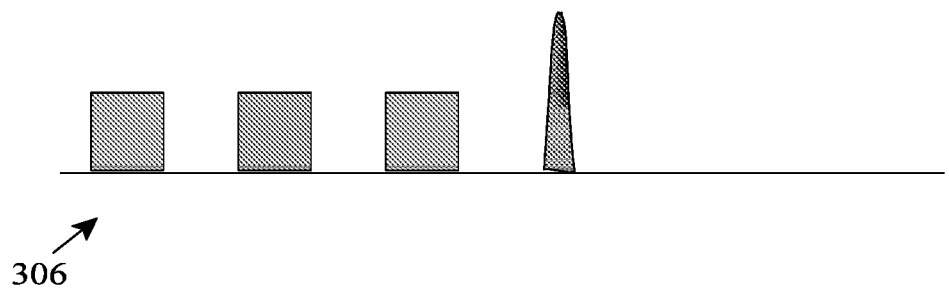

(FIGS. 6A, 6B, and 6C are hypothetical diagrams of exemplary pulse trains such as the invention might employ: these pulse trains are examples of individual pulses and thus are not the presently preferred embodiment, instead, these are "building blocks", low level pulse trains which might be used to create a variety of pulses as discussed above. Exemplary pulse trains 302, 304, and 306 have slightly different wave forms, amplitudes and frequencies from one another. Form 302 is a basic sine wave shape, repeated a minimal number of times, while 304 is a square wave. Wave from 306 is a further build: this wave form has one-half of each wave generated, followed by a different type of wave. Thus in sequence, 304 can be used to build 306, which itself is a small example step toward the true presently preferred embodiment shown in FIGS. 11 and 12.)

Returning to FIGS. 11 and 12, it will be understood that this is susceptible to changes from the present parameters. In addition to preset parameters, the timing and types and amounts of stimulation may be changed by a heuristic (learning) control module or by external wireless controls, for example, by a medical professional at a medical facility accessing the data files of the invention, analyzing the data including both input and output (stimulation and tension) and then altering the parameters wirelessly. The patient, who for example in the case of Cystic Fibrosis is quite likely to be a child, may never even be aware that they have, by remote wireless access and control, "been seen by the doctor", and that their treatment regime has been improved or altered. Thus there are three modes or more of control enabled by use of the control module linked to a mobile device: a first mode of control by means of manual control input to the mobile device, for example, when a patient is being seen or for a long-term patient who supervises some aspects of their own care, secondly an adaptive heuristic control by an artificial intelligence module loaded in the mobile device, in which the AI monitors and alters the parameters of the care given automatically and without human interference, and third, remote control from a remote location via communication with the mobile device, as discussed earlier, in which a medical professional might "call" or "text" (or more likely access by data network such as 4G), to control the mobile device and thus the control module. In the presently preferred embodiment, it is anticipated that combinations of these three modes will be most useful, with an AI app in the mobile device, human controls for the patient, and professional remote control all co-existing and being used routinely for the same patient but on different schedules.

This may wireless access of data and control of parameters may occur in bother or either of the FIG. 11 vibration phase or in the FIG. 12 cough phase.

Figure 7:
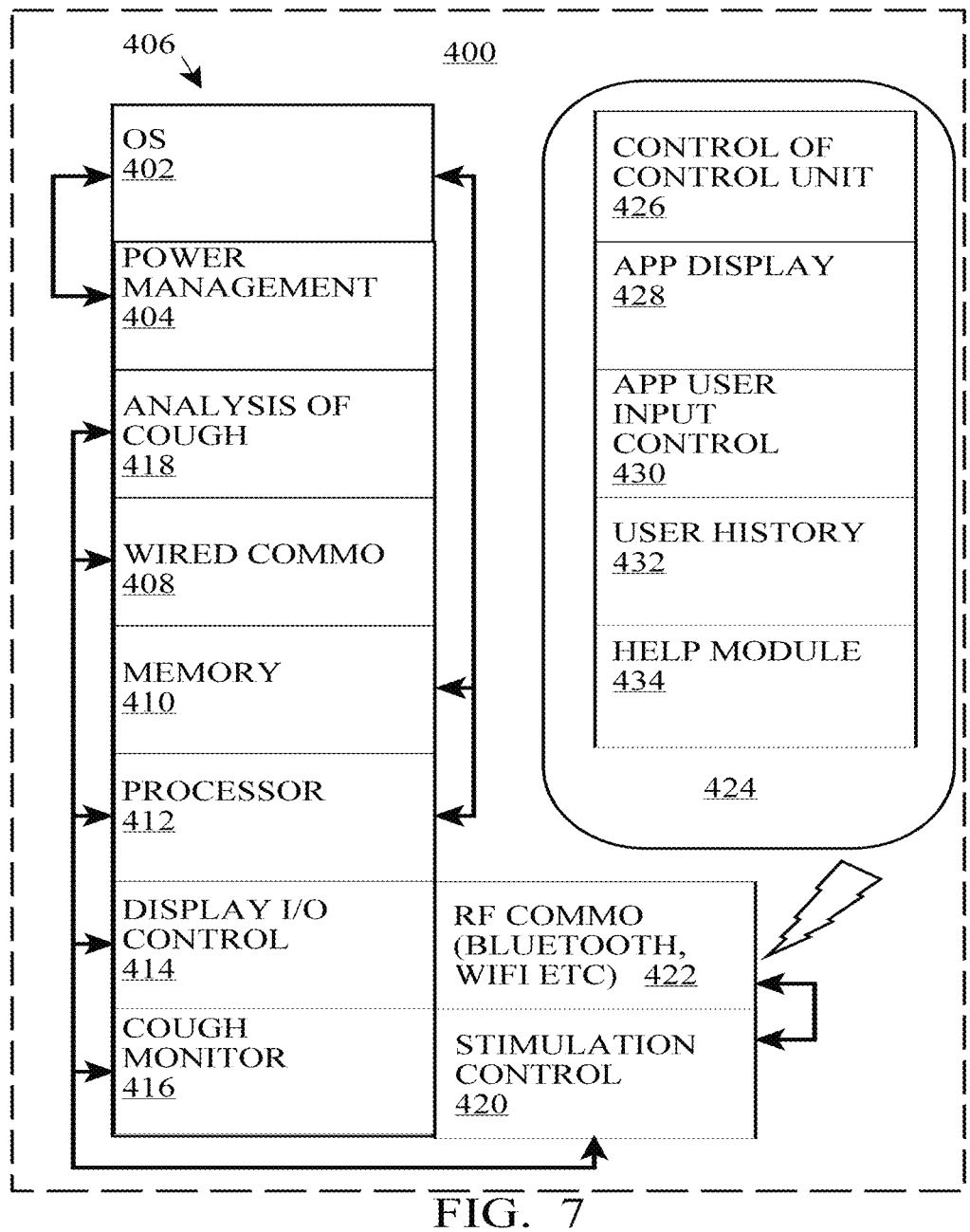
FIG. 7 is a block diagram of the modules of the invention in the control module and mobile device.

FIG. 7 is a block diagram of the modules of the invention in the control module and mobile device. System 400 may have two physical modules: the control module 406 (FIG. 4 item 114) and the mobile device 424 (FIG. 4 item 118). The may communicate either by wired communication or by means of wireless communication.

The control module 406 will have a number of modules and functionalities, which may be entirely mechanical, or partially programming stored in memory 410 and process by CPU 412. Operating system 402 may handle housekeeping chores such as inter-programming communications, power management 404, wired communication 408, access and management of the memory 410, as well as optional display screen control 414.

It will be appreciated that one preferred embodiment of the control module 406 will have a display screen, possibly a touch screen, allowing easy use of the control module without awkward controls and without requiring the mandatory use of a mobile device 424 as part of the system.

Cough monitor 416 will receive data from the sensor (see FIG. 4 item 120) and pass that information to analysis module 418, which may save it to memory 410 and/or send it via commo 422/408 to mobile device 424 to be saved there. If the analysis module 418 has determined that stimulation of muscles to vibrate or promote a cough is called for by pre-stored parameters or heuristic (learned) parameters, then stimulation control module 420 is activated to send via wired commo 408 (if the electrodes are wired) or RF commo module 422 (if the electrodes are also wireless) a command for a selected type of stimulation.

In general the RF communication module 422 may be used to receive instructions from, and provide data to the mobile device 424. Mobile device 424 will have at the top level a control module 426 which is distinct (see FIG. 7, item 406 versus item 426) from the largely hardware based control module 406. The "control function" 426 of the mobile device is obviously used to control the (largely hardware) control module 406, for example in embodiments of the control module 406 having no screen, or when the control module 406 (which is likely to be connected by leads and electrodes to the patient's body) is out of sight underneath clothing. Also, note that while the control module 114 (see FIG. 4) is depicted to be larger than the mobile device 118, it is most likely that the control module 114 will actually be much smaller than a mobile device, so as to make it easy and unobstrusive for the patient to wear. The smaller control module 114/406 in turn makes the use of a mobile device 118/424 more desirable as it will be easier to control: smaller units have less space for soft buttons, hard buttons and so on.

App display module 428 simply provides the patient or user with information while app user input control module 430 allows the user to actively enter control instructions into the control module 406 using the mobile device. User history module 432 may be useful in diagnostic or personal health scenarios, while help module 434 assists the user with control of the device, understanding of their medical situation and so on.

One possible embodiment of the invention is for the control module 406 to be an entirely electrical device with little or no programming (for example, no CPU, no memory, and all other functions based on hardware, with the various analysis and control modules such as 418, 416, and 420 moved to the mobile device 424. Mobile device 424 in turn may be the patient's own cellular telephone, with an app encompassing all of the electronic programming functions of the invention. In this embodiment, the hardware only control module 114/406 may still be sufficient to operate the system for secretion clearance and cough assistance for an extended period of time with nothing but electrical circuits for supervision by the unit.

FIG. 8 is a simple data structure as might be used by the device to assist therapeutic activities, to test the device or to optimize usage of the device for a given patient or condition. Event 500 might be a single instantiation of a data structure which has a new instance created and added to a database at each event 500. The trigger for the creation of the event entry 500 might be a physiological event such as a cough, a period of occluded breathing, a certain time of day, and so on and so forth. Time & Date field 502 might further include indicia of the duration of the event, autonomic cough monitored data 504 might provide the data collected by the sensor (see 120 on FIG. 4). Pulse train stimulation applied type 506, applied duration 508, frequency 510, and amplitude 512 are all typical information which might be stored to describe a single application of the electrodes to the muscles. Assisted cough monitored data 514 may provide the same sensor data as field 504, but for the time period of an assisted cough or an assisted clearance vibration, as a measurement against baseline of how effective any particular stimulation had been.

Figure 9:
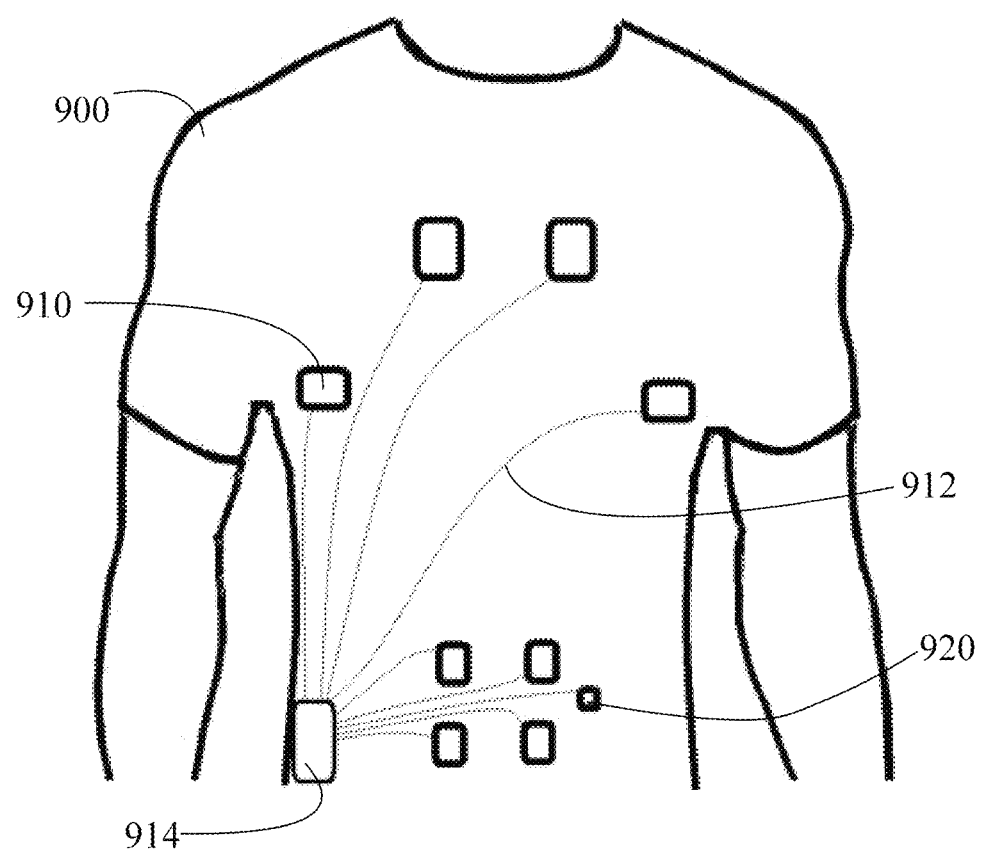
FIG. 9 is a transparent frontal view of a patient wearing the present invention device, showing the device worn inside of an ordinary t-shirt.

FIG. 9 is a transparent frontal view of a patient wearing the present invention device, showing the device worn inside of an ordinary t-shirt 900. Shirt 900 is chosen for the figure because it can be seen to be a very thin, small type, such as a child might wear while playing.

Despite the small size of the shirt 900, dermal electrode pads 910, leads 912, monitor 920 and even control module 914 can all fit inside of the shirt, against the wearer's body. Note that in the case of monitor 920 and electrodes 910, this may be a requirement for operation of the devices (the shirt might be an insulator or impedance).

Figure 10:
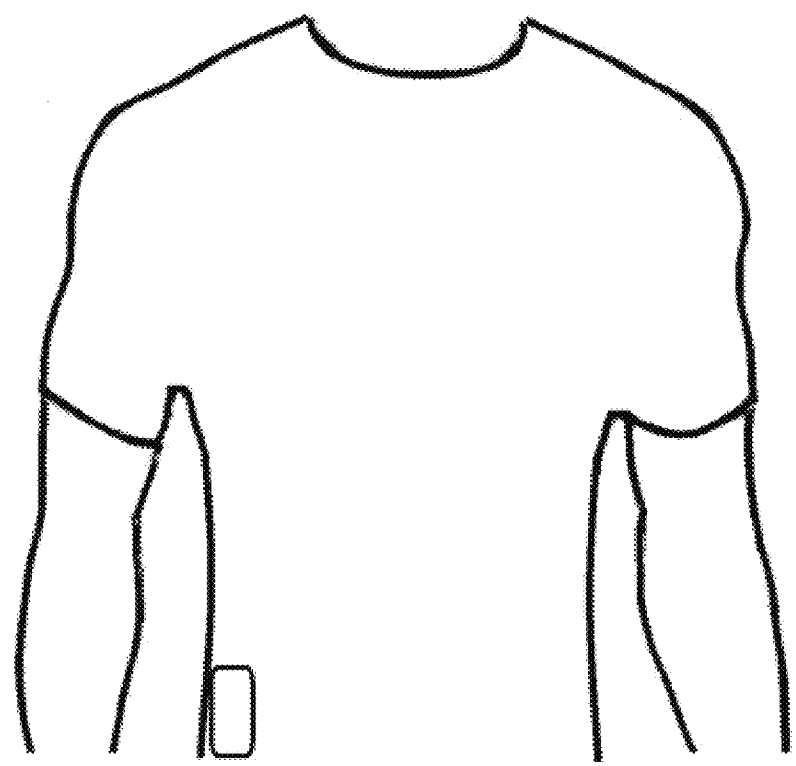
FIG. 10 is a non-transparent frontal view of a patient wearing the present invention, showing the actual front view (outside view) of the patient wearing a t-shirt, if they wear the control module visibly.

This aspect of the device has enormous benefits. The small size of the device means that the device can be easily and inconspicuously worn for greater mobility and especially greater social acceptance. FIG. 10 is a non-transparent frontal view of a patient wearing the present invention, showing the actual front view (outside view) of the patient wearing a t-shirt, if they wear the control module visibly. In this case, it may be seen that there is nothing but the small control module visible at all. A patient wearing the device with the control module outside of the shirt may appear to have nothing but a second mobile telephone or other consumer electronic device.

In embodiments, even the control module may be located inside of the shirt, or inside of a special garment.

Figure 13:
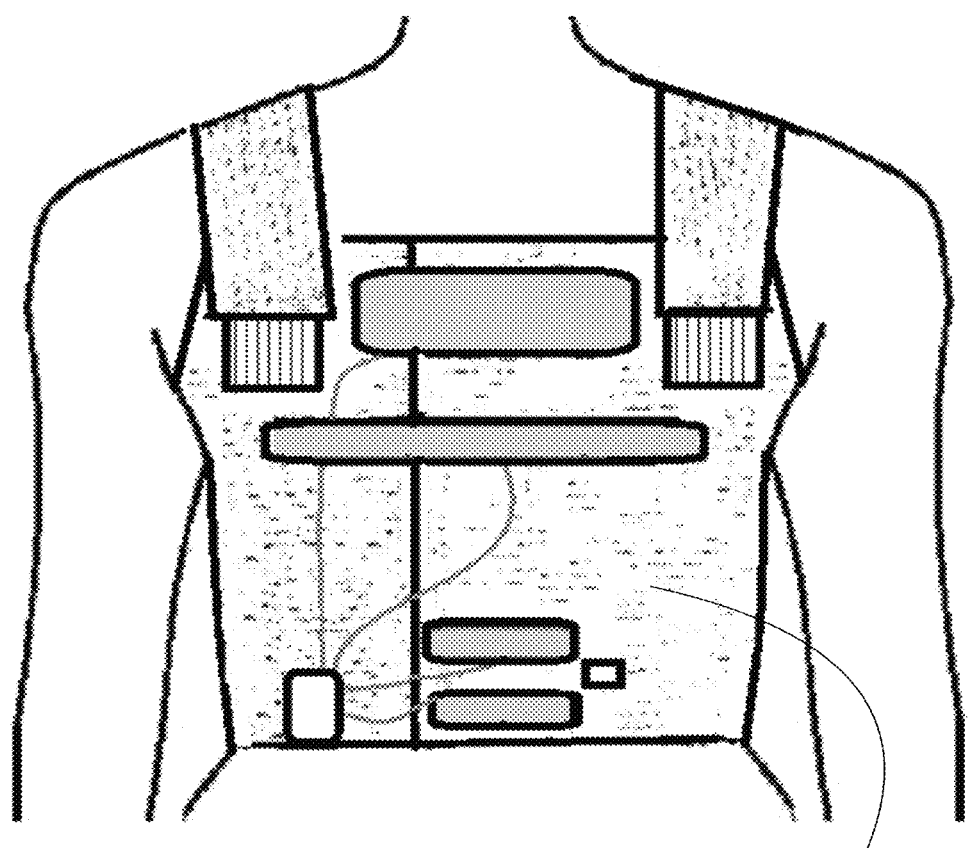
FIG. 13 is a view of a garment for wearing the invention in a snug and inconspicuous manner.

FIG. 13 is a view of a garment for wearing the invention in a snug and inconspicuous manner. Garment 1360 may be a simple band worn about the torso, such as seen in parts of this figure, or may be a more complete garment which covers most of the torso, much like a shirt, corset, tank top, or the like. In either case, the garment will hold snugly at least one electrode, rendering the electrode both secure and also less easy to see. This is another aspect of the invention which will be especially beneficial to youth, who may wish to avoid standing out amongst their peers.

In one important aspect, the garment may be used to hold one or more zone stimulators.

Figure 14:
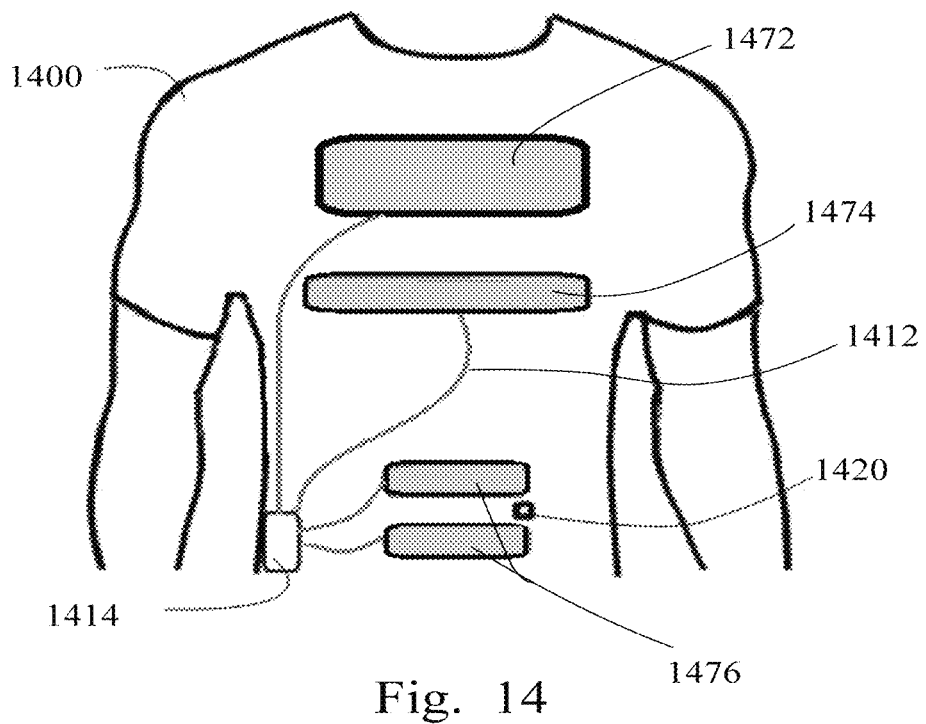
FIG. 14 is a transparent frontal view of a patient wearing a second embodiment of the present invention device, showing the device worn inside of an ordinary t-shirt with larger zone stimulators.
Figure 15:
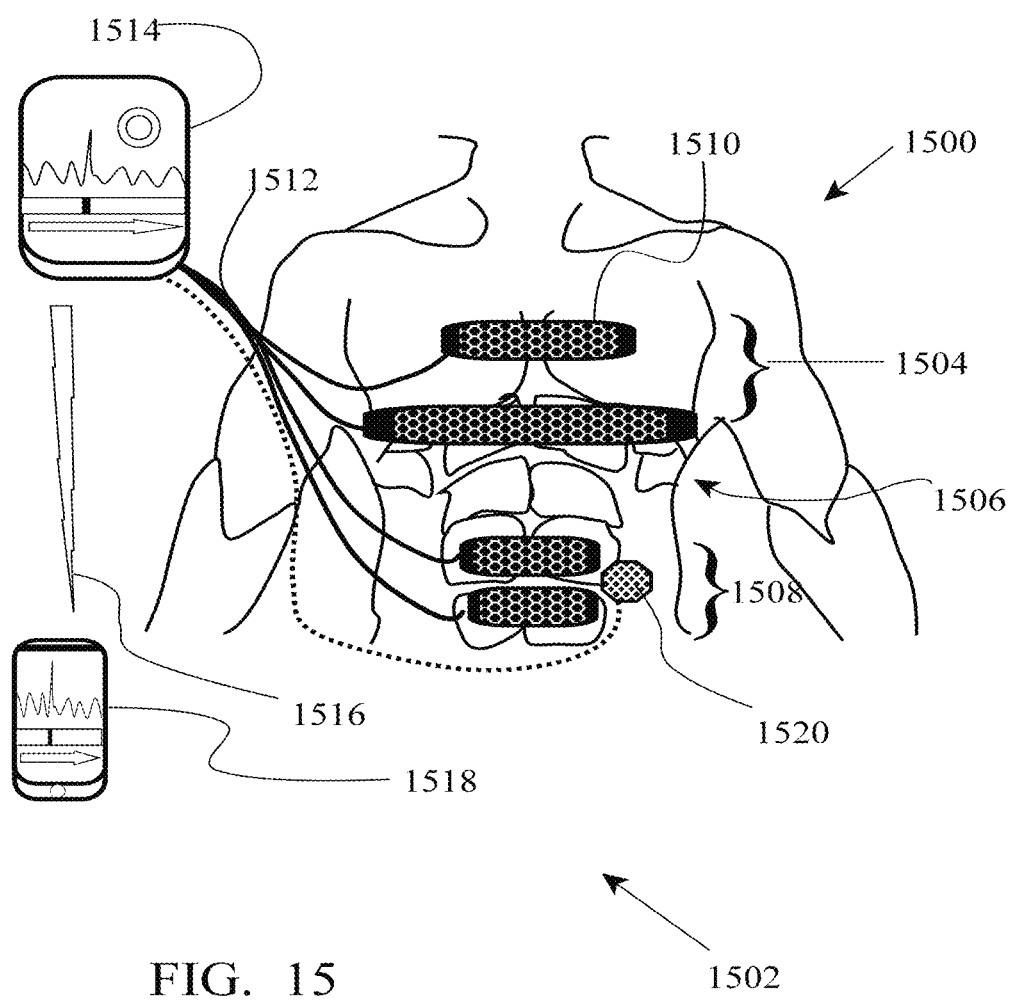
FIG. 15 is a front view of the second embodiment of the invention showing more detail of the muscle groups and the zone stimulators of the invention.

FIG. 14 is a transparent frontal view of a patient wearing a second embodiment of the present invention device, showing the device worn inside of an ordinary t-shirt, and with larger zone stimulators or zone electrodes instead of normal electrode pads. FIG. 15 is a front view of the second embodiment of the invention showing more detail of the muscle groups and the zone stimulators/large enough stimulators of the invention. FIG. 14 includes a shirt, whereas FIG. 15 includes more components and shows the muscle groups as well.

Testing of the invention has revealed that normally size electrodes (which tend to be perhaps one centimeter across in the center and only a few centimeters across total) may not be as effective at causing muscle response as much larger stimulators. Thus the term "large enough" electrodes is used herein to denote electrodes which are large enough to cause muscle response. The larger/large enough electrodes of the invention may be as much as several centimeters or several inches across, and may be used in multiples (for example 2 large electrodes in a single fabric enclosure) so as to function as even larger electrodes.

The present invention teaches a ZONAL stimulator pad which covers a substantial part of a muscle group, as shown in FIG. 14. Patient 1400/1500 has a control module 1414/1514 and a sensor/monitor 1420/1520 as previously described, as well as an RF (1516) control device 1518—but the stimulators are much different than the previous embodiment.

Each zone electrode may have one, or preferrably more than one electrode(s) (electrodes large enough to efficiently stimulate a large muscle) within it as an inner layer. The large electrodes within the zone electrode may be in contact with the skin directly, while the zone electrode has a large fabric enclosure as a second layer on the outside of the electrodes, insulating the electrodes (the fabric has insulating properties) from contact with shirts, other body parts, etc.

Zone "A" (pectoralis) stimulator pad 1472/1510 may be seen to be large enough to cover substantial parts of the pectoralis muscles 1504. Testing has shown that larger areas of stimulation provide better muscle response to the stimulation, and so the stimulator pad 1472 is sized to be as much as one quarter or one half or more of the area of the muscle group. In this case, one pad spans both pectoralis muscles.

Zone "B" (serratus) stimulator pad 1474 may be seen to span a much larger area than two small electrodes could, or even more than a whole group of normal sized electrodes could possibly cover. The zone stimulators of the invention stimulate larger areas of the muscles 1506, resulting in much larger stimulations of the various reflexes such as the vibration in the muscles 1506/1504.

Zones "C" and "D" (abdominal) stimulators 1476 stimulate the abdominal muscles 1508. These dermal zone stimulation pads (1510, etc) provide much better cough responses as well: the muscle is stimulated much more strongly than it would be with ordinary electrodes.

Leads 1512 connect the zonal stimulators/zone electrodes to their control devices.

The disclosure is provided to render practicable the invention by those skilled in the art without undue experimentation, including the best mode presently contemplated and the presently preferred embodiment. Nothing in this disclosure is to be taken to limit the scope of the invention, which is susceptible to numerous alterations, equivalents and substitutions without departing from the scope and spirit of the invention. The scope of the invention is to be understood from the appended claims.

Methods and components are described herein. However, methods and components similar or equivalent to those described herein can be also used to obtain variations of the present invention. The materials, articles, components, methods, and examples are illustrative only and not intended to be limiting.

Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art.

Having illustrated and described the principles of the invention in exemplary embodiments, it should be apparent to those skilled in the art that the described examples are illustrative embodiments and can be modified in arrangement and detail without departing from such principles. Techniques from any of the examples can be incorporated into one or more of any of the other examples. It is intended that the specification and examples be considered as exemplary only, with a true scope and spirit of the invention being indicated by the following claims.

What is claimed is:

1. A secretion clearance and cough assistance device configured for use by a patient having a body, skin, a mouth, airways, first, second, third, and fourth pairs of abdominal muscles, and chest muscles including pectoral muscles and serratus anterior muscles, such patient suffering from bodily secretions in such airways, the secretion clearance and cough assistance device comprising:
   a control module having operative electrical connections to a plurality of dermal electrodes configured to be attached to such skin of such patient, whereby the control module is in communication with the dermal electrodes, the control module configured so as to be worn on such patient body;
   a first one of the dermal electrodes configured to be disposed on such skin of such patient at one such chest muscle;
   a second one of the dermal electrodes configured to be disposed on such skin of such patient at one such abdominal muscle;
   each of the dermal electrodes configured to deliver a plurality of pulse trains to one such respective muscle;
   the control module having a stimulation module operative to send a first pulse train to such chest muscle and a second pulse train to such abdominal muscle;
   the first pulse train operative to stimulate such chest muscle so as to cause a first vibration of such chest muscle, the vibration of such chest muscle thereby causing a second vibration of such airways;
   the second pulse train operative to stimulate such abdominal muscle so as to stimulate at least one cough;
   whereby the second vibration loosens such bodily secretions in such airways and the at least one cough moves such bodily secretions toward such mouth of such patient.

2. The secretion clearance and cough assistance device of claim 1, configured for use with a shirt worn on such body by such patient, wherein:
   the control module, the dermal electrodes and the operative electrical connections are configured so as to be worn on such body concealed within such shirt, and the secretion clearance and cough assistance device further comprising a garment distinct from such shirt:
   the garment configured to be worn about such body by such patient, with the garment concealed within such shirt, and the garment concealing within itself the control module, dermal electrodes and operative electrical connections.

3. The secretion clearance and cough assistance device of claim 2, further comprising:
   a third one of the dermal electrodes configured to be disposed on such skin of such patient at a second such abdominal muscle;
   a fourth one of the dermal electrodes configured to be disposed on such skin of such patient at a third such abdominal muscle;
   a fifth one of the dermal electrodes configured to be disposed on such skin of such patient at a fourth such abdominal muscle;
   the control module further operative to send the second pulse train to such second, third and fourth abdominal muscles.

4. The secretion clearance and cough assistance device of claim 3, further comprising:
   a sixth one of the dermal electrodes configured to be disposed on such skin of such patient at a second such chest muscle;
   a seventh one of the dermal electrodes configured to be disposed on such skin of such patient at a third such chest muscle;
   an eighth one of the dermal electrodes configured to be disposed on such skin of such patient at a fourth such chest muscle;
   the control module further operative to send the first pulse train to such second, third and fourth chest muscles.

5. The secretion clearance and cough assistance device of claim 4, the first pulse train further comprising:
   a first group of pulses consisting of a plurality of individual pulses increasing in amplitude with time, the first group of pulses having a duration of 20 to 80 ms;
   a first time out period of 20 ms-250 ms during which no pulses are sent;
   repetitions of the first group of pulses and the first time out period for a vibration time period.

6. The secretion clearance and cough assistance device of claim 4, the second pulse train further comprising:

a second group of pulses consisting of a plurality of individual pulses increasing in amplitude with time, the second group of pulses having a duration of 500 ms to 900 ms;
a second time out period of 2 to 3 seconds during which no pulses are sent;
repetitions of the second group of pulses and the second time out period for a cough assist time period defined to last either until an autonomic cough occurs or for a period of time of no more than 10 seconds.

7. The secretion clearance and cough assistance device of claim 6, further comprising:
at least one cough sensor, the cough sensor in operative communication with the control module, the cough sensor configured to be disposed on such skin of such patient;
the control module further comprising an analysis module operative to receive a data from the cough sensor and analyze the data to determine if such patient is exhibiting an autonomic cough and if such patient is exhibiting an autonomic cough, the control module further operative to send the first pulse train.

8. The secretion clearance and cough assistance device of claim 7, further comprising:
an RF communication module;
the control module having a non-volatile memory and a central processor unit, the analysis module stored in the non-volatile memory, the control module having a start button operative to activate the secretion clearance and cough assistance device to begin an operating cycle, using a first set of preset operating parameters also stored in the non-volatile memory;
a mobile device having an operative RF connection to the RF communication module of the control module and further having a touch screen operative to display a set of data collected by the device and enable control of the secretion clearance and cough assistance device;
the start button further operative to establish the operative RF connection to the mobile device;
the mobile device having a module operative to provide wireless control of the operation of the control module;
the mobile device operative to collect data, provide for wireless setup and wireless maintenance of the secretion clearance and cough assistance device.

9. The secretion clearance and cough assistance device of claim 8, wherein the mobile device is operative to provide control of the control module by one mode selected from the group consisting of: manual control input to the mobile device and the control module, manual control input to the mobile device and from the mobile device to the control module, adaptive heuristic control by an artificial intelligence module loaded in the mobile device and the control module, adaptive heuristic control by an artificial intelligence module loaded in the mobile device and from the mobile device to the control module, remote control from a remote location via communication with the mobile device and from the mobile device to the control module, and combinations thereof.

10. A method of secretion clearance and cough assistance configured for use by a patient having skin, a mouth, airways, first, second, third, and fourth pairs of abdominal muscles, and chest muscles including pectoral muscles and serratus anterior muscles, such patient suffering from bodily secretions in such airways, the secretion clearance and cough assistance, comprising the steps of:
sending a first pulse train controlled by a first set of parameters to a first electrode configured to be disposed on such skin of such patient at one such chest muscle, the first pulse train operative to stimulate such chest muscle so as to cause a first vibration of such chest muscle, the vibration of such chest muscle thereby causing a second vibration of such airways;
whereby such second vibration loosens such bodily secretions in such airways;
sending a second pulse train to a second electrode configured to be disposed on such skin of such patient at a first such abdominal muscle, the second pulse train operative to stimulate such abdominal muscle so as to stimulate at least one assisted cough;
whereby the at least one assisted cough moves such bodily secretions toward such mouth of such patient.

11. The method of secretion clearance and cough assistance of claim 10, further comprising:
monitoring such patient and sending a data set to an analysis module;
determining by means of the analysis module when such patient is exhibiting an autonomic cough and when such patient is exhibiting an autonomic cough, sending the first pulse train.

12. The method of secretion clearance and cough assistance of claim 11, further comprising:
wirelessly accessing the analysis module from a remote location; and
providing the data set to the remote location.

13. The method of secretion clearance and cough assistance of claim 12, further comprising:
wirelessly altering the first set of parameters from the remote location.

14. A secretion clearance and cough assistance device configured for use by a patient having a body, skin, a mouth, airways, first, second, third, and fourth pairs of abdominal muscles, and chest muscles including pectoral muscles and serratus anterior muscles, such patient suffering from bodily secretions in such airways, the secretion clearance and cough assistance device comprising:
a control module having operative electrical connections to a plurality of zone group stimulators configured to be attached to such skin of such patient, whereby the control module is in communication with the zone group stimulators, the control module small enough to be worn on such patient body;
a first one of the zone group stimulators configured to be disposed on such skin of such patient at at least one such chest muscle;
a second one of the zone group stimulators configured to be disposed on such skin of such patient at at least one such abdominal muscle;
each of the zone group stimulators configured to deliver a plurality of pulse trains to one such respective muscle;
the control module having a stimulation module operative to send a first pulse train to such chest muscle and a second pulse train to such abdominal muscle;
the first pulse train operative to stimulate such chest muscle so as to cause a first vibration of such chest muscle, the vibration of such chest muscle thereby causing a second vibration of such airways;
the second pulse train operative to stimulate such abdominal muscle so as to stimulate at least one cough;
whereby the second vibration loosens such bodily secretions in such airways and the at least one cough moves such bodily secretions toward such mouth of such patient.

15. The secretion clearance and cough assistance device of claim 14, the first pulse train further comprising:
- a first group of pulses consisting of a plurality of individual pulses increasing in amplitude with time, the first group of pulses having a duration of 20 to 80 ms;
- a first time out period of 20 ms-250 ms during which no pulses are sent;
- repetitions of the first group of pulses and the first time out period for a vibration time period;
- the second pulse train further comprising:
- a second group of pulses consisting of a plurality of individual pulses increasing in amplitude with time, the second group of pulses having a duration of 500 ms to 900 ms;
- a second time out period of 2 to 3 seconds during which no pulses are sent;
- repetitions of the second group of pulses and the second time out period for a cough assist time period defined to last either until an autonomic cough occurs or for a period of time of no more than 10 seconds.

* * * * *